United States Patent [19]

Wallace et al.

[11] Patent Number: 4,966,161

[45] Date of Patent: Oct. 30, 1990

[54] APPARATUS FOR CONTINUOUSLY MEASURING INTRACOMPARTMENTAL PRESSURE WITHIN A BODY CAVITY

[75] Inventors: William D. Wallace, Salt Lake City; Christopher A. Cutler, Centerville, both of Utah

[73] Assignee: Utah Medical Products, Midvale, Utah

[21] Appl. No.: 331,436

[22] Filed: Mar. 31, 1989

[51] Int. Cl.$^5$ .................................................. A61B 5/03
[52] U.S. Cl. ..................................... 128/748; 128/778
[58] Field of Search ............... 128/748, 775, 778, 645, 128/672, 674, 675

[56] References Cited

U.S. PATENT DOCUMENTS

| | | | |
|---|---|---|---|
| 3,038,465 | 6/1962 | Allard et al. | 128/2.05 |
| 3,380,488 | 4/1968 | Sadove et al. | 128/215 |
| 3,559,643 | 2/1971 | Panaler | 128/214.4 |
| 3,651,807 | 3/1972 | Huggins | 128/214.4 |
| 3,710,781 | 1/1973 | Hutchins et al. | 128/2.05 |
| 3,877,429 | 4/1975 | Rasumoff | 128/214.4 |
| 3,946,724 | 3/1976 | La Balme | 128/2.05 |
| 4,030,481 | 6/1977 | Hill | 128/2 S |
| 4,136,681 | 1/1979 | Hon | 128/2 R |
| 4,155,364 | 5/1979 | Boxer | 128/349 |
| 4,166,469 | 9/1979 | Littleford | 128/784 |
| 4,191,193 | 3/1980 | Seo | 128/675 |
| 4,243,050 | 1/1981 | Littleford | 128/784 |
| 4,252,131 | 2/1981 | Hon et al. | 128/748 |
| 4,274,423 | 6/1981 | Mizuno et al. | 128/675 |
| 4,282,881 | 8/1981 | Todd et al. | 128/675 |
| 4,306,562 | 12/1981 | Osborne | 128/348 |
| 4,325,387 | 4/1982 | Helfer | 128/748 |
| 4,407,296 | 10/1983 | Anderson | 128/675 |
| 4,456,013 | 6/1984 | De Rossi et al. | 128/675 |
| 4,476,871 | 10/1984 | Hon | 128/642 |
| 4,509,370 | 5/1985 | Hirschfeld | 73/705 |
| 4,517,984 | 5/1985 | Perlin | 128/642 |
| 4,576,181 | 3/1986 | Wallace et al. | 128/675 |
| 4,588,398 | 5/1986 | Daugherty et al. | 604/265 |
| 4,601,706 | 7/1986 | Aillon | 604/122 |
| 4,603,699 | 8/1986 | Himpens | 128/632 |
| 4,608,986 | 9/1986 | Beranek et al. | 128/786 |
| 4,610,256 | 9/1986 | Wallace | 128/675 |
| 4,611,600 | 9/1986 | Cohen | 128/687 |
| 4,640,983 | 2/1987 | Comte | 174/119 |
| 4,650,472 | 5/1987 | Bates | 604/158 |
| 4,679,567 | 7/1987 | Hanlon et al. | 128/675 |
| 4,685,469 | 8/1987 | Keller | 128/675 |
| 4,722,730 | 2/1988 | Levy et al. | 604/118 |
| 4,754,753 | 7/1988 | King | 128/699 |
| 4,785,822 | 11/1988 | Wallace | 128/675 |
| 4,873,986 | 10/1989 | Wallace | 128/775 |

OTHER PUBLICATIONS

"The Use of Catheter-Tip Pressure Transducers for the Measurement of Intrauterine Pressure in Labour-A Significant Advance", (date unknown).

(List continued on next page.)

Primary Examiner—Lee S. Cohen
Assistant Examiner—S. Getzow
Attorney, Agent, or Firm—Workman, Nydegger & Jensen

[57] ABSTRACT

An apparatus for monitoring intracompartmental pressures, such as intrauterine pressure, is disclosed. The apparatus comprises a catheter having a first chamber formed in the interior of the catheter tip which is in amniotic fluids communications with the fluids contained in the uterus. A second chamber is defined by a lumen of the catheter and is filled with air. The lumen extends the length of the catheter from the first chamber at the tip of the catheter to a diaphragm of a pressure transducer located at the end of the catheter. Thus, an air column is formed in the second chamber defined by the lumen. The relative volumetric cubic capacity of the first and second chambers is such that, under maximum pressures which are within expected ranges, the trapped air column prevents any liquid fluids from entering the second chamber. Also, provided is a valve which in a first or "zero" position causes both sides of the pressure transducer diaphragm to be placed at atmospheric pressure. In a second or "monitoring" position the valve places a one side of the diaphragm in communication with the intrauterine pressures transmitted through the lumen and a side of the diaphragm is vented to atmosphere. A second or infusion lumen may also be provided in the catheter to allow for infusion of fluids into and/or withdrawal of fluid samples from the uterus.

35 Claims, 4 Drawing Sheets

OTHER PUBLICATIONS

"Intracardiac Catheter Tip Piezoresistive Pressure Gauge," The Review of Scienfific Instruments, 31.9, 987–991 (1960).

"An IC Piezoresistive Pressure Sensor for Biomedical Instrumentation," EE Transactions on Biomedical Engineering, BME-20: 101–109 (1973).

"Miller Mikro-Tip Catheter Transducers," a company advertising brochure, 1–14 (date unknown).

"Catheter Tip Pressure Transducers," a company brochure prepared by Gaeltec (date unknown).

Honeywell advertising brochure (date unknown).

"A stable UltraMiniature Catheter-Tip Pressure Transducer," (1973).

"The Effect of Oxytocin Infusion on Uterine Activity Levels in Slow Labour," British Journal of Obstetrics and Gynaecology, (1985).

"Detection of the Fetal ECG During Labour by an Intrauterine Probe," Journal of Biomedical Engineering (1988).

"Oesophageal Probe for Heart and Temperature Monitoring During Anaesthesia", Medical & Biological Engineering & Computing, May 1982.

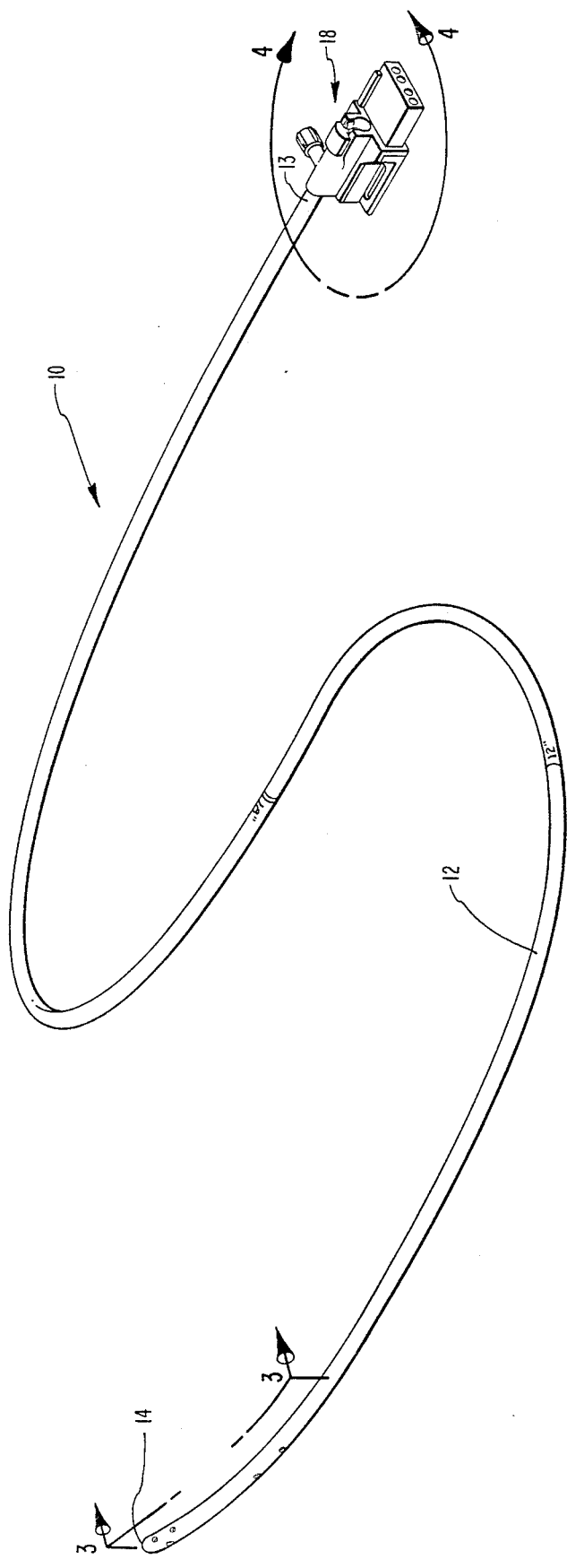
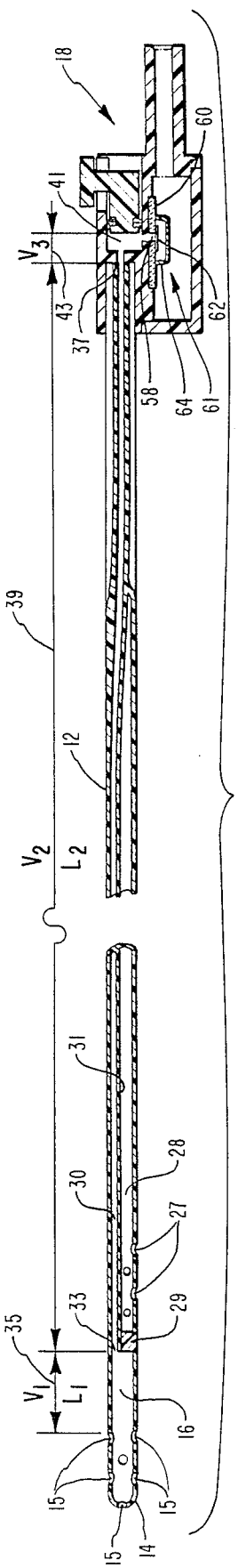
FIG. 1
FIG. 2

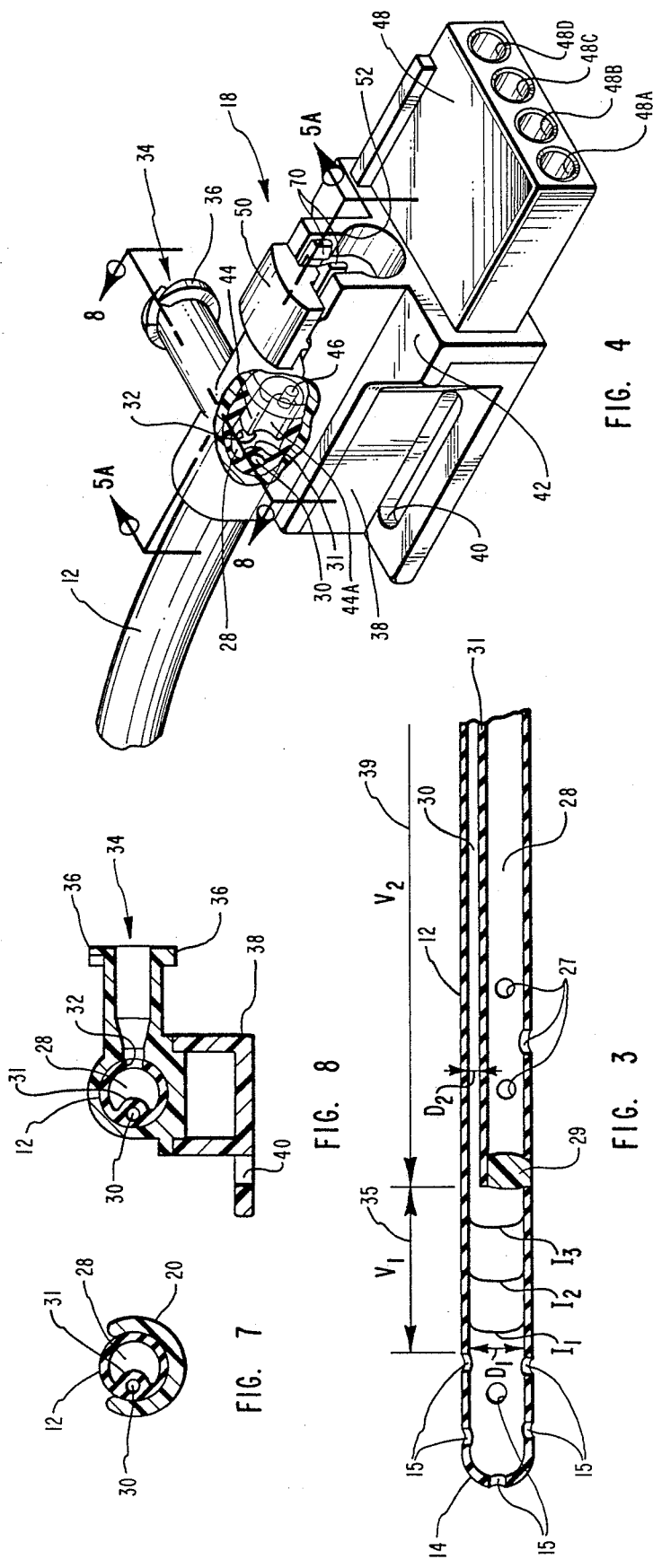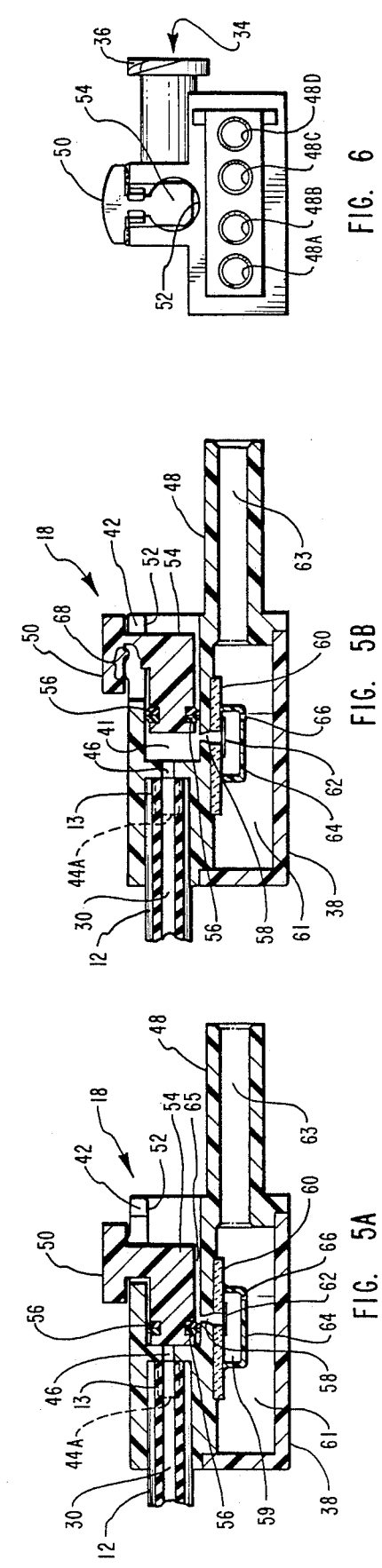

APPARATUS FOR CONTINUOUSLY MEASURING INTRACOMPARTMENTAL PRESSURE WITHIN A BODY CAVITY

BACKGROUND

1. The Field of the Invention:

This invention relates to apparatus used to monitor intracompartmental pressures within a body. More particularly, the present invention is directed to an apparatus for use in direct continuous measurement and monitoring of intrauterine pressure during labor and childbirth.

2. The Prior Art:

Each year, approximately 3.5 million children are born within the United States. In order to assist physicians in treating a mother and child approaching childbirth, monitoring devices are commonly used during the final stages of labor to monitor the mother's uterine contractions. Such monitoring devices can quickly provide the physician with information about the rate, duration, and intensity of the mother's uterine contractions and, when a fetal heart monitor is used, the effect of the contractions on the fetal heart rate. This information can help the physician ensure that oxygen and nutrients are being properly transferred from the mother to the fetus during labor and childbirth and can help the physician identify potential problems before they become life-threatening.

It is often the case that uterine contractions are monitored using devices which can be secured externally to the surface of the mother's abdomen. For example, a pressure sensitive button called a tocotransducer is often secured to the mother's abdomen to provide information about the frequency and duration of the uterine contractions.

In many cases, externally secured monitoring devices can provide sufficient information to enable a physician to treat the mother and child during labor and childbirth. It will be appreciated, however, that the use of external monitoring devices may give rise to large measurement errors in some cases due to extraneous noise and/or movement by the mother. In many labor and birthing situations, and particularly where there is a significant risk of complications, a physician may wish to have more accurate measurements than can be obtained using external monitoring devices.

In order to obtain more reliable and accurate information about the mother's uterine contractions, a physician will often initiate intrauterine pressure monitoring. In addition to providing information about the rate and duration of the uterine contractions, intrauterine pressure monitoring can also provide accurate information about the intensity of the uterine contractions. Importantly, since the uterine pressure is being measured directly, errors in measurement due to extraneous noise and movement by the mother are less likely than with external monitoring devices.

One of the most widely used techniques for intrauterine pressure measurement and monitoring uses a liquid-filled catheter inserted into the uterus and then connected externally to a pressure transducer. In using this technique, a rigid guide tube is inserted just inside the mother's cervix. A catheter is then threaded through the guide tube until it extends into the uterus approximately 15 to 20 centimeters (cm). This catheter is filled with a sterile liquid solution, such as, for example, a sterile saline solution. Once the catheter is in place, the guide tube is removed from the cervix and slid away from the mother along the catheter.

After the in-dwelling catheter is positioned as described above, the other end of the catheter is hydraulically coupled to a pressure transducer typically mounted to a bedside IV stand or pole. The pressure transducer is often used with a disposable dome that fits over the tranducer diaphragm. The dome has two ports, one on the side and one vertical. The side port is connected to the in-dwelling liquid-filled catheter after it is primed with sterile solution. The other port is generally used for zero balancing and calibration. The pressure transducer is connected to a monitor device near the patient. Typical monitor devices include cathode ray tube display devices, digital display and/or recording devices, printers, and plotters.

In addition to the proper set-up of the measurement equipment in the above-described manner, when using a liquid-filled catheter, it has been conventional practice to prime the catheter with a sterile solution so that any air bubbles within the catheter are removed and a continuous liquid column is provided from the pressure transducer to the tip of the catheter within the uterus. Then, when the mother's uterus contracts, the increased intrauterine pressure displaces the liquid within the catheter, and the pressure transducer thereby detects a change in the intrauterine pressure. The pressure transducer generates electrical signals proportional to the detected intrauterine pressure, and such signals are then amplified and displayed by the monitor device. Usually, the monitor device is used to display the mother's intrauterine pressure as a function of time, often along with the fetal heart rate, and this data can then be used by the physician and other medical personnel to appropriately diagnose and treat the mother and child.

While the foregoing technique for monitoring intrauterine pressure is widely used and under proper circumstances can produce reliable measurements, there are a number of disadvantages associated with the technique.

One disadvantage of the above-described technique is the time required to fill and prime the catheter with the sterile solution. Particularly in a critical situation, this procedure uses up valuable time, and is somewhat cumbersome since the transducer is connected by a relatively long length of liquid-filled tubing running from the mother over to the bedside pole-mounted transducer. Furthermore, sometimes an air bubble will enter the open end of the catheter. In such cases, it has been the common practice to flush the catheter with sterile solution to remove the air bubble. Occasionally the catheter is replaced altogether under such circumstances.

BRIEF SUMMARY AND OBJECTS OF THE INVENTION

In view of the present state of the art, it is a primary object of the present invention to provide an improved apparatus for monitoring intracompartmental pressure.

It is another object of the present invention to provide a disposable apparatus for monitoring intracompartmental pressure which is safe, accurate, and economical.

It is another object of the present invention to provide an apparatus for intracompartmental pressure monitoring which does not require a liquid column to couple the intracompartmental pressure to a pressure transducer.

Another important object of the present invention is to provide an intracompartmental pressure monitoring apparatus wherein both sides of the diaphragm of the pressure transducer may be conveniently vented to a reference pressure such as atmospheric pressure whenever it is desired to zero the transducer.

It is also an object of the present invention to provide an apparatus for intrauterine pressure monitoring which eliminates the complexity of having to run a liquid-filled tube from the catheter to a pole-mounted transducer.

It is yet another object of the present invention to provide an intrauterine monitoring apparatus which also allows fluid samples to be withdrawn from, and fluids to be infused into, the uterus.

Additional objects and advantages of the invention will be apparent from the description and claims which follow, or may be learned by the practice of the invention.

Briefly summarized, the foregoing objects and advantages are realized in an improved apparatus for monitoring intracompartmental pressures. In the presently preferred embodiment, the apparatus comprises a catheter adapted for insertion into a patient's uterus. The catheter is provided with one or more apertures located near the distal tip of the catheter such that a first chamber formed in the interior of the distal catheter tip is in fluid communication with the amniotic fluids of the uterus. Accordingly liquid fluids will enter the first chamber and will form a liquid column therein having a liquid-air interface. A second chamber, which is filled with air, is defined by an interior lumen that extends the length of the catheter up to the first chamber located at the distal tip of the catheter. An air column is formed by air trapped in the second chamber. The relative volumetric capacity of the first and second chambers is such that, under maximum uterine pressures found within expected ranges, the trapped air column will tend to minimize the liquid column in the first chamber thereby minimizing hydrostatic pressure error resulting therefrom, and will also tend to prevent amniotic fluid from entering the second chamber. Uterine pressure is transmitted from the partially liquid-filled first chamber, through the air-filled column of the second chamber, to the diaphragm of the transducer.

In the described embodiment, the proper volumetric ratio between the first and the second chambers is obtained by making the cross-sectional area of the second chamber much smaller and its length much longer than the corresponding area and dimensions of the first chamber. Other applications of the present invention may require a volumetric ratio other than those represented herein. Importantly, regardless of the relative volumetric capacities of the two chambers, they are preferably designed so that, at the expected maximum intracompartmental pressure, the liquid column which has entered the first chamber is minimized as noted above and the liquid-air interface is prevented from entering the second chamber.

Using an air column rather than a liquid-filled column to couple the intrauterine pressure to the pressure transducer diaphragm provides advantages of ease of use and lower cost when compared to previously available intrauterine pressure monitoring apparatus. Also, since the air column used in transmitting the intrauterine pressure is an excellent electrical insulator, patient safety is increased because the patient is electrically isolated from the electrical currents found in the pressure transducer.

The present invention may also comprise means for infusing fluids into and/or withdrawing fluid samples from the uterus which, for example, may comprise an infusion or second lumen included in the catheter. The present invention also preferably comprises a means for zeroing the pressure transducer. Zeroing of the pressure transducer is carried out after the catheter has been inserted into the uterus and the appropriate monitoring device connected to the pressure transducer.

In the preferred embodiment of the invention, the means for zeroing the transducer comprises a sliding valve which, in a first or "zero" position, causes both sides of the transducer diaphragm to be placed at atmospheric pressure. In a second or "monitoring" position the slide valve places one side of the diaphragm in fluid communication with the second chamber and the other side of the diaphragm is vented to a reference pressure such as atmosphere, i.e., pressure in the case of intrauterine pressure monitoring.

BRIEF DESCRIPTION OF THE DRAWINGS

In order to more fully understand the manner in which the above-recited objects and advantages of the invention are obtained, a more particular description of the invention will be rendered by reference to the presently preferred embodiment or presently understood best mode thereof which is illustrated in the appended drawings. Understanding that these drawings depict only one embodiment of the invention and are therefore not to be considered limiting of its scope, the presently preferred embodiment and the presently understood best mode of the invention will be described with additional detail through use of the accompanying drawings in which:

FIG. 1 is a perspective view illustrating the presently preferred embodiment of the apparatus of the present invention.

FIG. 2 is a cross-sectional view of the embodiment shown in FIG. 1 taken along its entire length.

FIG. 3 is a cross-sectional view of the tip of the described embodiment taken along line 3—3 of FIG. 1.

FIG. 4 is a partially cut-away perspective view of the portion of the apparatus encompassed by line 4—4 of FIG. 1.

FIGS. 5A and 5B are cross-sectional views of the described embodiment taken along line 5A—5A of FIG. 4.

FIG. 6 is an elevated end view of the embodiment shown in FIG. 4.

FIG. 7 is a cross-sectional view of the described embodiment taken along line 7—7 of FIG. 9.

FIG. 8 is a cross-sectional view of the described embodiment taken along line 8—8 of FIG. 4.

DETAILED DESCRIPTION OF THE PREFERRED EMBODIMENT

Figure 9:
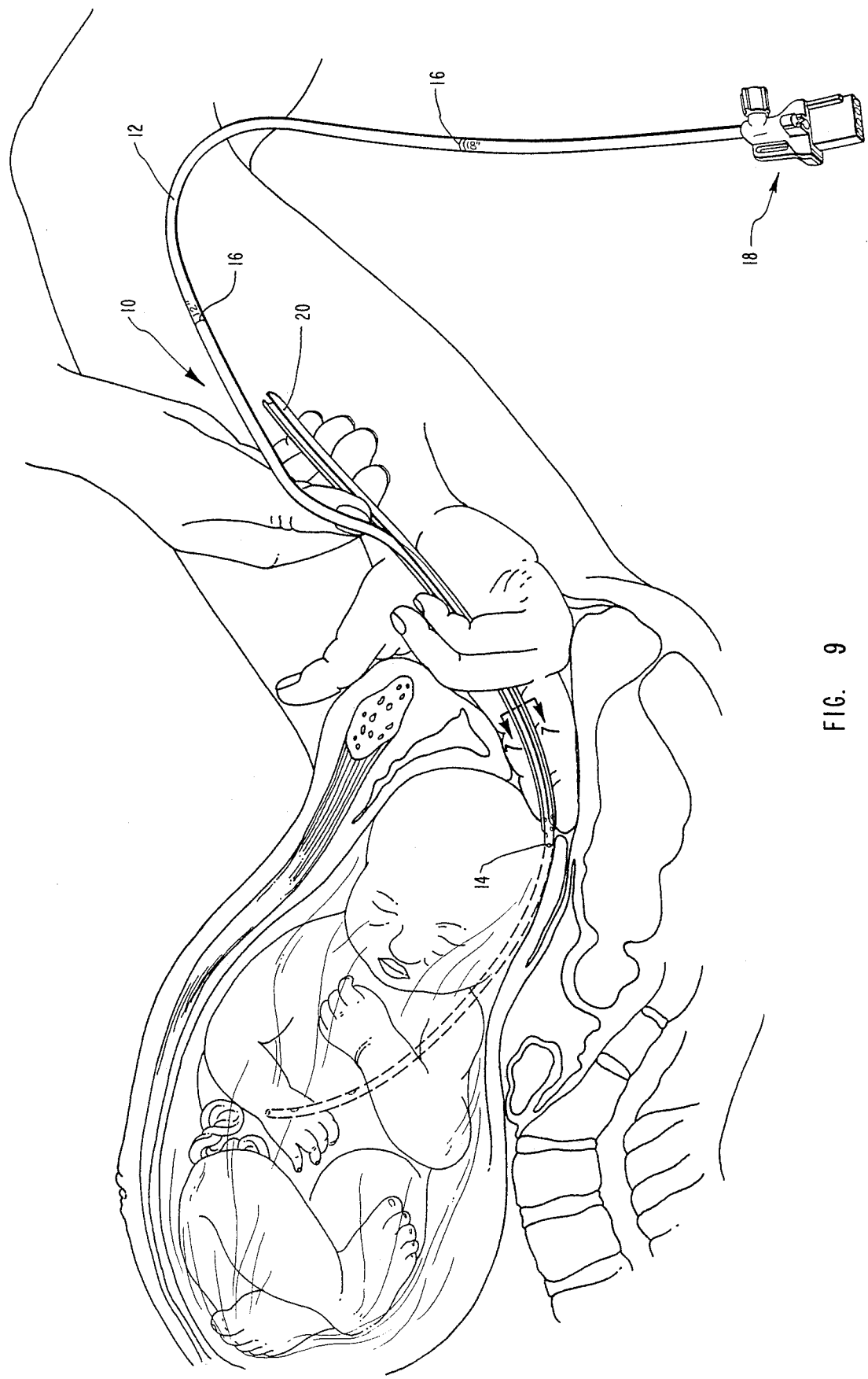
FIG. 9 is a cross-sectional view illustrating the procedure for inserting the apparatus of the described embodiment into a uterus.

It will be readily appreciated that the components of the present invention, as generally described and illustrated in the figures herein, could be arranged and designed in a wide variety of different configurations. For example, although the embodiment described herein is particularly adapted for measuring intrauterine pressure, the present invention may be incorporated into embodiments adapted to other intracompartmental pressure monitoring applications, including but not limited to, intra-articular, esophageal, intra-intestinal, intra-vesicular and/or intracranial monitoring.

Referring first to FIG. 1, the overall apparatus 10 of the present invention is illustrated. As hereinafter more fully described, the apparatus is comprised of a pressure-sensing means for insertion into a body cavity (for example, a uterus) so as to detect intracompartmental fluid pressures therein. The pressure-sensing means comprises first chamber means for defining the first volume which is in fluid communication with the fluid pressures exerted by a liquid contained within the body cavity and a second chamber means for defining a second volume which is air-filled and is in fluid communication with the first chamber means. The apparatus further comprises pressure transducer means for generating an electrical signal proportional to fluid pressure communicated by the pressure-sensing means to the pressure transducer. Preferably, the ratio of the first volume to the second volume is such that, at maximum fluid pressures exerted within the body cavity, the liquid column formed by liquid entering the first chamber means forms a liquid-air interface which will tend to be minimized so as to minimize hydrostatic pressure errors resulting from the liquid column, and such that the liquid-air interface of the liquid column will be prevented from entering the second chamber means.

In the illustrated embodiment of FIG. 1, the pressure-sensing means is comprised of a catheter 12 which has a gently rounded distal tip 14 fashioned for ease of insertion into a patient's uterus. As will be appreciated, the pressure-sensing means is not intended to be necessarily limited in its form to that of a catheter but may take other forms depending upon the particular application for which the apparatus is designed.

Positioned at the proximal end 13 of the catheter 12 is a connector means generally designated 18, for housing a pressure transducer and for providing electrical connection between the transducer and an electrical cable connected to a monitor, and for providing fluid connection to permit infusion and sampling of intracompartmental fluids, as desired, and as hereinafter more fully explained. The catheter 12 may be fabricated from materials known to those skilled in the art in accordance with the concepts taught herein and so as to have an appropriate amount of stiffness to allow insertion into the uterus.

Referring now to FIG. 2, a more detailed description of the internal structure of the catheter 10 will be provided. FIG. 2 is a cross-sectional view taken along the length of the catheter 12 and connector means 18. The interior of catheter 10 is formed so as to provide the aforementioned first chamber means defining a first volume and the second chamber means for defining a second volume. In the illustrated embodiment, the first chamber means is formed at the distal tip 14 of catheter 10 and is comprised of that portion of the interior space 16 located at the distal tip 14 of catheter 10 which corresponds to the length $L_1$. That portion of the interior space 16 which corresponds to length $L_1$ defines a first volume $V_1$ as schematically indicated at 35 which is in fluid communication with the amniotic fluid of the uterus through the apparatus 15 which are formed at the distal tip 14. Accordingly, as the uterus contracts, amniotic fluid is forced into interior space 16 and as schematically represented at $I_1$ in FIG. 3, a liquid-air interface is formed by the liquid amniotic fluids which enter the interior space 16. As hereinafter more fully explained, the liquid-air interface may be forced further into the chamber 16 which defines the volume $V_1$ as the intrauterine pressure is increased.

In the illustrated embodiment of FIG. 2, the second chamber means which defines a second volume is comprised, for example, of a first interior lumen 30 which extends along the length of the catheter 10 from the proximal end 13 of catheter 10 and which terminates at a distal end 33 of the first lumen 30 at the point where the volume $V_1$ begins. The distal end 33 of lumen 30 opens into the chamber 16 defining the volume $V_1$ so as to be in fluid communication therewith. In this manner, the second chamber means defines a second volume $V_2$ as schematically indicated at 39 which is in fluid communication with the first chamber means.

Importantly, the volume $V_2$ which is defined by the first interior lumen 30 is air filled. As hereinafter more fully explained, this advantageously eliminates the need which has heretofore existed in connection with prior art apparatus and methods for filling the catheter with a liquid, and also provides the important advantage of electrically isolating the pressure transducer from the amniotic fluid and hence from the patient.

As explained previously, the use of a liquid-filled column has been common in the art as a means to couple pressure from within a body cavity to an external pressure transducer. For example, the dynamic range required by direct arterial blood pressure monitoring (0 Hz to 40–50 Hz) requires that a liquid column be used to couple the pressure transducer to the arterial pressure. As is commonly known in the art, the introduction of air bubbles into a liquid column tends to damp the dynamic response of the system causing inaccurate reproduction of the arterial pressure wave form and introducing unacceptable errors into the signal.

Based on this experience, many in the art have tended to assume that a liquid-filled catheter free of such entrapped air must be used to monitor nearly all intracompartmental pressures, even intrauterine pressure. However, as noted above, the use of a liquid-filled catheter has several drawbacks.

Significantly, the present invention takes advantage of the discovery that the dynamic range required to accurately monitor and reproduce intrauterine pressure wave forms is much less than that required to accurately monitor arterial pressure wave forms. The same may be true for monitoring intracompartmental pressures of other body cavities such as those mentioned earlier.

The dynamic range of a pressure monitoring system required for intrauterine pressure monitoring applications may have a high-frequency cut-off of, for example, 1 Hz–2 Hz. If a dynamic range of only 0 Hz–2 Hz is required, then an appropriately configured air column is readily able to effectively couple intrauterine pressure to an external pressure transducer. The potential advantages, as noted above, of using an air column to couple a pressure transducer to an intracompartmental pressure have heretofore not been recognized in the art.

The present invention, as embodied in the catheter represented in FIG. 2, advantageously utilizes an air column to couple a pressure transducer to an intracompartmental pressure. However, proper utilization of the air column, which is contained in the volume $V_2$ of the interior lumen 30, depends upon a proper design of the volumes $V_1$ and $V_2$. Specifically, as hereinafter more fully explained in connection with FIGS. 2 and 3 taken together, the ratio of the first volume $V_1$ to the second volume $V_2$ is preferably such that, at maximum fluid pressures exerted during a contraction of the uterus, the amniotic fluid entering the chamber 16 which defines volume $V_1$ will form a liquid column having the aforementioned liquid-air interface I. The liquid column will tend to be minimized and the liquid-air interface I will be prevented from entering the volume $V_1$ defined by the first interior lumen 30. This advantageously minimizes any hydrostatic pressure error that would otherwise be caused by the liquid column in $V_1$. The volume $V_1$ is also referred to herein as the "transition volume" because of the liquid column with its liquid-air interface which is formed within volume $V_1$, so that there is a transition from a partially liquid-filled volume to a partially air-filled volume, which transition occurs within the volume $V_1$.

Three distinct volumes are indicated in FIG. 2. The first volume $V_1$ or transition volume occupies a portion of the interior space 16 of catheter 12 between the most proximal apertures 15 and the distal end 33 of lumen 30, as previously noted and as schematically shown by arrow 35.

Volume $V_2$, also referred to herein as the "pressure coupling volume," extends from the transition volume $V_1$ to the proximal end 13 of catheter 12, as schematically shown at arrow 39. A second lumen 28 (which may be used to infuse and/or sample amniotic fluid) is not involved in the pressure monitoring function of the apparatus and will be explained in greater detail below. It should be noted that in order to clearly show the pertinent interior structure of catheter 12 in FIG. 2, the opposite ends 14 and 13 of catheter 12 have been radially twisted 90 degrees with respect to each other.

The third volume $V_3$ schematically represented at arrow 43 in FIG. 2 includes the fluid space 41 found in the connector means 18 which provides fluid communication between lumen 30 and the pressure transducer 62 mounted on substrate 61. It should be noted that, due to its small size when compared to $V_1$ and $V_2$, $V_3$ contributes negligibly to the overall design and may, in some cases, be ignored. Thus, as defined herein, the ratio of the first and second volumes as noted above is intended to mean the ratio of $V_1$ to $V_2$, and/or in the alternative, the ration of $V_1$ to $V_2$ and $V_3$ taken together. As further represented in FIG. 2, two lengths $L_1$ and $L_2$ are associated with volumes $V_1$ and $V_2$, respectively.

The relationship between the described volumes must be carefully chosen in accordance with the inventive concepts taught herein in order to provide an embodiment which effectively couples intracompartmental pressure such as intrauterine pressure to an external pressure transducer.

Reference will now be made to FIG. 3 to further explain the principles used in designing the structure of the apparatus 10. When the tip 14 of the catheter 12 is inserted into a patient's uterus, amniotic fluid will be forced through apertures 15 into $V_1$.

The diameter $D_1$ of interior chamber 16 defining $V_1$ (the shape of the catheter 12 is preferably cylindrical) is small enough so that a liquid-air interface I is formed within volume $V_1$ such as that represented at $I_1$. An idealized representation of the meniscus-like shape of the liquid-gas interface is illustrated at I.

The position within chamber 16 of the liquid-air interface represented at $I_1$ corresponds to a condition when uterine contractions are mild. The liquid-air interface $I_1$ is kept near the distal end of chamber 16 due to the counter-pressure of the air column trapped within the volume $V_2$ provided by the second chamber defined by lumen 30.

The position of interface $I_1$ in chamber 16 is also determined by the pressure within the uterus. When the patient is not experiencing a contraction, the intrauterine pressure will generally be just above a selected reference pressure, such as atmospheric pressure (which is the air pressure within volume $V_2$ of lumen 30 and volume $V_1$) so that interface $I_1$ advances only slightly into chamber 16.

As the patient experiences a contraction, pressure within the uterus may increase to 100 mmHg above atmospheric pressure and the liquid-air interface may advance into chamber 16 to the position shown at $I_2$. If pressure within the uterus increases to, for example, a maximum design value of 200 mmHg above atmospheric pressure, the liquid-air interface may advance to the position shown at $I_3$.

It will be appreciated that since the number of gas molecules contained in $V_1$, $V_2$, and $V_3$ does not change, according to Boyle's Law the change in pressure experienced in the uterus will in turn be exerted on transducer 62 by means of the air column contained in the second chamber defined by lumen 30 and space 41.

Importantly, embodiments incorporating the teachings of the present invention should preferably be designed so as to minimize the liquid column (and thense any hydrostatic pressure error) and so as to avoid forcing the liquid-air interface I into the second chamber defined by lumen 30. Due to the small diameter $D_2$ and long length $L_2$ of lumen 30, if liquid enters into lumen 30, capillary action may cause the liquid to be drawn further into the lumen 30 hampering the accuracy of the pressure monitoring function.

Accordingly, to avoid these problems, the relationship of volumes $V_1$, $V_2$ and $V_3$ must be properly defined in order to properly design the apparatus for a given application. In the described embodiment, $V_2$ preferably is designed so that it has a much smaller cross-sectional area than the cross-sectional area of volume $V_1$. Thus, the diameter $D_2$ of lumen 30 should be much less than the diameter $D_1$ of the chamber 16. Further, the length of lumen 30 represented at $L_2$ should be much longer than the length $L_1$ of chamber 16.

An equation can be derived from Boyle's Law which describes the change in position of the liquid-air interface ($I_1$, $I_2$, and $I_3$ in FIG. 3) when pressure within the uterus (or other body compartment) is altered. It should be appreciated that when monitoring intrauterine pressure, the pressure experienced within the uterus is generally higher than atmospheric pressure. In other intracompartmental pressure monitoring applications, the intracompartmental pressure may be lower than atmospheric pressure and consideration must be given to this condition. Moreover, while differences in temperature, for example, the difference between body temperature and room temperature, have some effect on the accuracy on the pressure readings obtained using the principles of the invention, such effects on accuracy are generally so small as to be negligible in most design applications.

Equation (1) provided below describes $\Delta I$ (the changing position of the liquid-air interface represented in FIG. 3) in terms of other parameters of the system and the surrounding environment.

$$\Delta I = 4/(\pi D_1^2)(V_1 + V_2 + V_3)(1 - P/(P + \Delta P)) \text{ where} \quad (1)$$

ΔI = change in position of liquid-air interface
$V_1$ = volume of first chamber 16
$D_1$ = diameter of the first chamber 16
$V_2$ = volume of second chamber or lumen 30
$V_3$ = volume of space 41 in the connector means 18
P = absolute atmospheric pressure
ΔP = intracompartmental pressure applied to liquid-air interface As mentioned, the value obtained for ΔI under expected maximum intracompartmental pressures must be less than the length ($L_1$) of the first chamber 16 which defines the transition volume $V_1$.

In Examples 1 and 2 below, the presently preferred dimensions for the described embodiment are shown and calculations are carried out to show the appropriate ΔI values obtained. All of the parameters are the same in Example 1 and Example 2 with the exception of the change in intrauterine pressure, which is 100 mmHg in Example 1 and 200 mmHg in Example 2. As can be seen by the results of the examples, the presently preferred values provide excellent results.

| Example 1 | | |
|---|---|---|
| π | 3.14159 | |
| $D_2$ | 0.032 | diameter of catheter (inches) |
| $L_2$ | 30.5 | length of catheter (inches) |
| $V_3$ | 0.15 | volume of transducer and connector (ml) |
| $V_2$ | 0.40 | volume of catheter (ml) |
| $D_1$ | 0.093 | diameter of catheter tip (inches) |
| $L_1$ | 1.5 | length of catheter tip (inches) |
| $V_1$ | 0.17 | volume of catheter tip (ml) |
| $V_1 + V_2 + V_3$ | 0.72 | total air volume (ml) |
| ΔP | 100 | change in pressure (mmHg) |
| P | 760 | atmospheric pressure (mmHg) |
| Results: | | |
| ΔI | 1.40 | change in length (inches) |
| % error | 1.40% | |

| Example 2 | | |
|---|---|---|
| π | 3.14159 | |
| $D_2$ | 0.032 | diameter of catheter (inches) |
| $L_2$ | 30.5 | length of catheter (inches) |
| $V_3$ | 0.15 | volume of transducer and connector (ml) |
| $V_2$ | 0.40 | volume of catheter (ml) |
| $D_1$ | 0.093 | diameter of catheter tip (inches) |
| $L_1$ | 1.5 | length of catheter tip (inches) |
| $V_1$ | 0.17 | volume of catheter tip (ml) |
| $V_1 + V_2 + V_3$ | 0.72 | total air volume (ml) |
| ΔP | 200 | change in pressure (mmHg) |
| P | 760 | atmospheric pressure (mmHg) |
| Results: | | |
| ΔI | 1.35 | change in length (inches) |
| % error | 1.26% | |

The apparatus of the present invention further comprises an infusion and sampling means for infusing fluid into a body cavity such as a uterus and for withdrawing fluid samples from the body cavity, as desired. In the illustrated embodiment of FIGS. 2 and 3, the infusion sampling means comprises a second lumen 28 formed through the interior of catheter 12. The second lumen 28 is coextensive in length with the first lumen 30 and is sealed at the distal end thereof as illustrated at plug 29 to prevent fluid communication between the chamber 16 and the second lumen 28. Catheter 12 also comprises a plurality of apertures 27 formed therein for providing fluid communication between amniotic fluid in the uterus and the second lumen 28.

As best illustrated in FIGS. 7 and 8, the first lumen 30 is comprised of a cylindrical tube 31 which is formed along the interior wall of the catheter 10 and the second lumen 28 is comprised of the remaining space between the cylindrical tube 31 and the interior wall of catheter 12. As shown best in FIGS. 5A and 5B, the proximal end 13 of catheter 12 is secured within a corresponding channel of the connector means 18. The channel serves as a means for receiving and securing the proximal end 13 of catheter 13 in a fluid-tight fit.

With continued reference to FIGS. 5A and 5B, the pressure transducer means of the apparatus of the present invention is illustrated in greater detail. In the embodiment there illustrated, the pressure transducer means is comprised of piezoresistive semiconductor integrated circuit 62 which is mounted on a substrate 60 and which is enclosed by a protective cap 64. The piezoresistive semiconductor integrated circuit 62 is provided with a diaphragm for deflection in response to fluid pressures exerted on one side of the diaphragm whereas the other side of the diaphragm is continuously vented to a reference pressure, such as atmospheric pressure in the case of an apparatus for intrauterine pressure monitoring. Further detail with respect to the substrate 61, transducer 62 and protective cap 64 are illustrated and described in U.S. Pat. No. 4,576,181 which is incorporated herein by reference.

With reference to FIGS. 4, 5A and 5B taken together, the connector means 18 of the apparatus is shown in the illustrated embodiment as comprising, for example, an upper half 42 which is connected to a lower half 38. The substrate 60, transducer 62 and protective cap 64, as best shown in FIGS. 5A and 5B, are housed within the space 61 formed between the upper and lower halves 38 and 42 of the housing. As illustrated in FIG. 5B, one side of the pressure transducer 62 is placed in fluid communication with the air column of lumen 30 by means of the opening 58 formed through substrate 60 and a wall of the upper half 42 of the housing, and thence through the space 41 and small cylindrical bore 46 which communicates directly with lumen 30. The other side of the transducer diaphragm is continuously vented to atmospheric pressure by means of a small hole 66 formed through the protective cap 64, and thence through the space 61 and the space 63 which is also used for providing electrical connection to an electrical cable as hereinafter more fully explained. In the illustrated embodiment, the small opening 66 in cap 64 in combination with the space 61 and space 63 defined by the housing serve as a means for continuously venting one side of the diaphragm of the pressure transducer to a reference pressure such as atmospheric pressure.

In order to zero the pressure transducer 62 so as to establish an accurate baseline from which intracompartmental pressures can be referenced, the connector means 18 of the apparatus comprises a valve means for selective positioning between a first and a second position. When the valve means is in the first position, one side of the diaphragm of the pressure transducer is vented through the connector means 18 to the reference pressure and when the valve means is in the second position, that same side of the diaphragm is then placed in fluid communication with the fluid pressures which are to be monitored and which are communicated through the second chamber defined by lumen 30.

As shown in FIGS. 4, 5A and 5B, in the illustrated embodiment, the valve means is comprised of a slide valve 54 that is seated within a channel 52 formed in the housing. The slide valve 54 has a knob 50 at its upper end to permit movement back and forth of the slide valve 54 within the channel 52.

As shown in FIGS. 5A and 5B, one end of the slide valve 54 is provided with a sealing gasket 56 and provides a fluid-tight seal at that end of the slide valve 54 with respect to channel 52. Accordingly, when slide valve 54 is in a first or "zero" position as shown in FIG. 5A, the sealing gasket 56 provides a barrier which prevents fluid communication between the lumen 30 and the space 58. Accordingly, in this position the transducer 62 is vented to the reference pressure (atmospheric pressure in the case of intrauterine monitoring) through the small space 65 and thence through the channel 52. As shown best in FIG. 6, slide valve 54 has a generally square cross-sectional shape as opposed to the circular shape of channel 52 so that adequate venting is assured. Since the other side of transducer 62 is continuously vented to atmospheric pressure as described above, when the slide valve 54 is in the position of FIG. 5a, both sides of the transducer are being vented to the reference or atmospheric pressure so that any offset which occurs by reason of the electric componentry of the transducer 62 can be detected and corrected by the monitor.

When the slide valve 54 is moved to the second or "monitoring" position as illustrated in FIG. 5B, the sealing gasket 56 then provides a flight-tight barrier which prevents venting of one side of the transducer 62 through the space 65 to the reference or atmospheric pressure. Thus, in the second position as illustrated in FIG. 5B, one side of the transducer 62 is in fluid communication with lumen 30 by means of the small bore 46, space 41 and the small opening 58 whereas the other side of the transducer 62 is vented to the reference or atmospheric pressure. Thus, in the second position as shown in FIG. 5B, the transducer 62 will continuously monitor intrauterine pressure communicated through lumen 30 and will detect the deflections exerted on the diaphragm of the transducer 62 so as to output a proportional electrical signal. The transducer 62 is electrically connected to an electrical cable through the connectors 48A-D provided in the housing.

In order to prevent inadvertent movement of the slide valve 54 from one position to the other, the connector means 18 also comprises a means for releasably retaining slide valve 54 in whichever position to which it has been selectively moved. In the illustrated embodiment, the means for releasably retaining the slide valve in the selected position is provided by a ridge and valley defeat structure which is indicated at 68 in FIG. 5B, and also by a pair of arms which are indicated at 70 in FIG. 4.

The connector means 18 of the apparatus also comprises a fluid infusion port generally designated at 34 and which, in the illustrated embodiment (see FIGS. 4 and 8) is shown as a conventional male luer connector 36. As shown best in FIG. 8, samples of amniotic fluid can be withdrawn from or, as desired, saline or other sterile fluids may be infused into the uterus through the fluid port 34 and a corresponding aperture 32 formed through the side wall of catheter 12.

The channel of the housing which serves as the above-described means for receiving and securing the proximal end 13 of catheter 12 is comprised of means for orienting the second or infusion lumen 28 in a selected position relative to the fluid port 34 so that the aperture 32 formed through the side wall of cather 12 will be assured of providing the required fluid communication between the lumen 28 and the fluid port 34. As shown best in the partial cutaway portion of FIG. 4, in the illustrated embodiment, the means for orienting lumen 28 to the selected position for aligning aperture 32 with fluid port 34 is comprised of a keyway 44A which has a cross-sectional shape corresponding to that of the lumen 28 so as to be inserted into the lumen 28 when the proximal end 13 of catheter 12 is inserted into the channel of the housing. The keyway 44A is situated in the channel of the housing. The small cylindrical bore 46 (see also FIGS. 5A and 5B is provided through a wall of the housing which is situated at the end of the channel in which the catheter 12 is inserted. Accordingly, by means of the keyway 44a, the required orientation of catheter 12 as illustrated in FIG. 8 is accomplished so that aperture 32 is in alignment with the fluid port 34.

The manner in which the described embodiment may be used is illustrated, for example, in FIG. 9, which shows an intrauterine application. The patient should be in the dorsal lithotomy position, the uterine membrane ruptured, and the cervix adequately dilated. Using a guide tube 20 as shown to guide the catheter 12, it is inserted into the cervix until it is well into the amniotic space for intrauterine monitoring, as shown by the dashed-line representation. Insertion should be performed carefully and gently, without force. Any cervical quadrant may be used. Once the catheter has been fully inserted, the guide tube may be withdrawn and the catheter 12 removed through the slot (see also FIG. 2) in the guide tube 20 using the thumb as shown in FIG. 9.

FIG. 7 provides a cross-sectional view showing the presently preferred shape of the guide tube 20 with the catheter body resting therein. The guide tube 20 may be fabricated from one of several materials known and available in the art for such purposes. If desired, markings 16 (see FIGS. 9 and 10) may be placed on catheter 12 at suitable intervals (for example, one mark at 12 inches (30 cm) and two marks at 18 inches (45 cm)), to assist the physician or nurse in determining depth of insertion.

Figure 10:
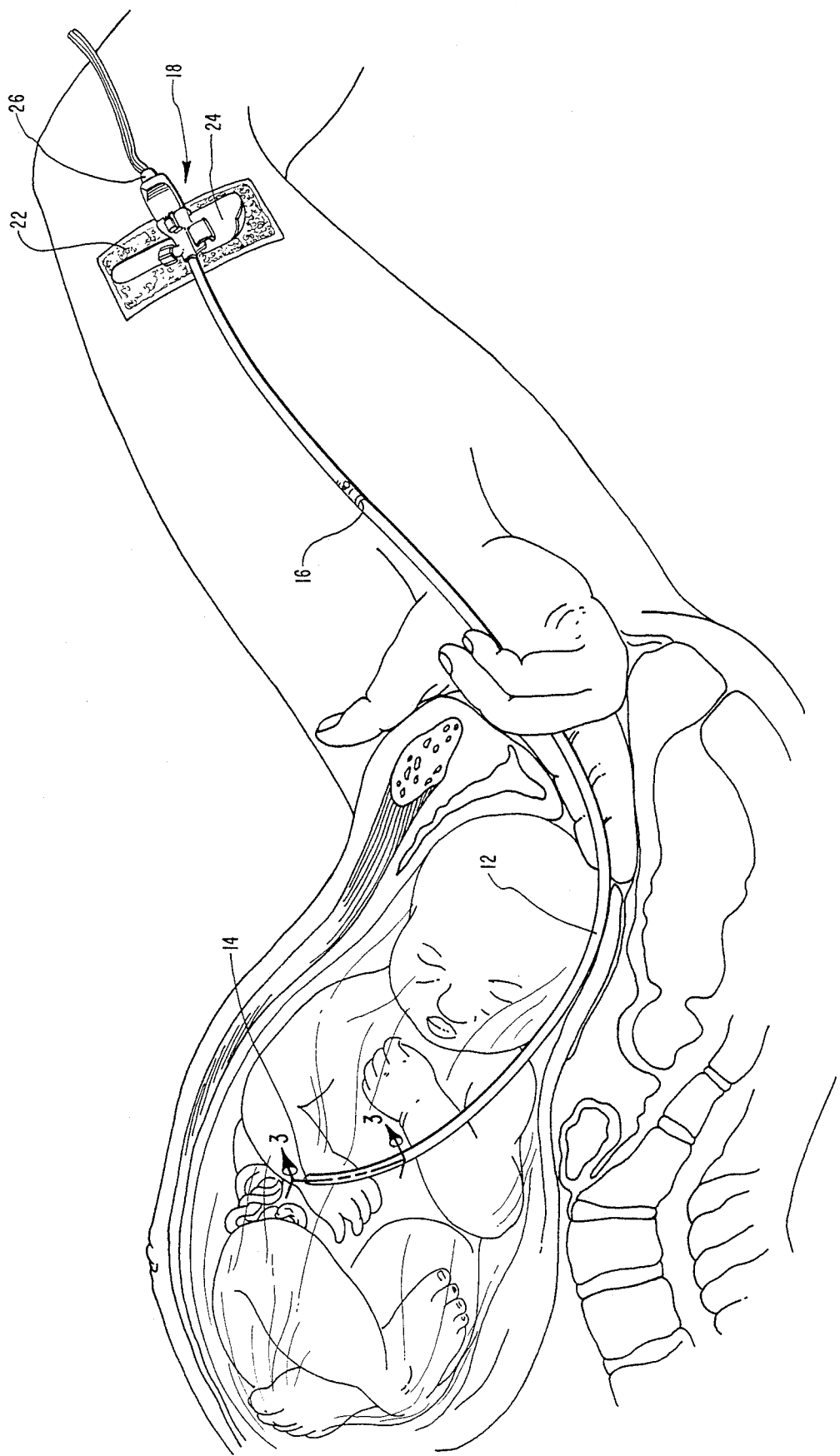
FIG. 10 is a cross-sectional view showing one possible positioning of the apparatus of the described embodiment within the uterus.

FIG. 10 illustrates one possible final placement of the catheter 12 within the uterus. Once insertion of the catheter has been completed, a hook and pile type fastener (such as is available under the trademark VELCRO) may be used to attach the connector means 18 to the patient's body. In FIG. 10, an adhesive backed pad of pile component 22 is shown attached to the inside of the patient's thigh with a strap 24, fabricated from the hook component, inserted through a slot 40 provided in connector 18. Also, in FIG. 10 electrical cable 26 has been attached to connector means 18.

The invention may be embodied in other specific forms without departing from its spirit or essential characteristics. The described embodiment is to be considered in all respects only as illustrative and not restrictive. The scope of the invention is, therefore, indicated by the appended claims, rather than by the foregoing description. All changes which come within the meaning of range of equivalency of the claims are to be embraced within their scope.

What is claimed is:

1. An apparatus for continuously measuring intracompartmental fluid pressures exerted by a liquid contained within a body cavity, comprising:
   pressure-sensing means for insertion into said body cavity so as to detect said intracompartmental fluid pressures therein, said pressure-sensing means comprising first chamber means for defining a first volume which is in fluid communication with said liquid such that said liquid will enter said first chamber means and form a liquid column therein having a liquid-air interface, and further comprising second chamber means for defining a second volume which is air-filled and is in fluid communication with said first chamber means;
   pressure transducer means attached to said pressure sensing means for generating an electrical signal proportional to fluid pressure communicated by said pressure-sensing means to said pressure transducer means; and
   wherein a ratio is defined by said first and second volumes such that the ratio of said first volume to said second volume is such that, at maximum fluid pressures exerted within said body cavity, said liquid column in said first chamber means will tend to be minimized so as to minimize hydrostatic pressure error resulting therefrom and such that said liquid-air interface will be prevented from entering said second chamber means.

2. An apparatus as defined in claim 1 wherein said pressure-sensing means comprises a catheter.

3. An apparatus as defined in claim 2 wherein said second chamber means comprises a lumen formed in the interior of said catheter and extending throughout a substantial portion of the length thereof, said lumen terminating at a distal end thereof, and wherein said first chamber means comprises at least a portion of the interior space of said catheter defined between said distal end of said lumen and a distal end of said catheter.

4. An apparatus as defined in claim 3 wherein said distal end of said catheter comprises a plurality of apertures formed therein for providing fluid communication between said liquid in said body cavity and said portion of said interior space of said catheter which forms said first chamber means.

5. An apparatus as defined in claim 3 further comprising infusion and sampling means for infusing fluid into said body cavity and for withdrawing fluid samples from said body cavity, as desired.

6. An apparatus as defined in claim 5 wherein said infusion and sampling means comprises a second lumen formed through the interior of said catheter.

7. An apparatus as defined in claim 6 wherein said second lumen is coextensive in length with said lumen of said second chamber means.

8. An apparatus as defined in claim 7 wherein said second lumen is sealed at a distal end thereof to prevent fluid communication between said first chamber means and said second lumen.

9. An apparatus as defined in claim 8 wherein said catheter comprises a plurality of apertures formed therein for providing fluid communication between said liquid in said body cavity and said second lumen.

10. An apparatus as defined in claim 7 wherein said other lumen comprises a cylindrical tube formed along an interior wall of said catheter, and wherein said second lumen is formed by the remaining space between said cylindrical tube and said interior catheter wall.

11. An apparatus as defined in claim 10 wherein said ratio of said first and second volumes is selected in accordance with the following expression wherein $\Delta I$ is a value that indicates that the liquid-air interface will not enter said second chamber means:

$$\Delta I = 4/(\pi D_1^2)(V_1 + V_2)(1 - P/(P + \Delta P))$$

where
$\Delta I$ is the change in position within said first chamber means of said liquid-air interface;
$V_1$ is the volume of said first chamber means;
$D_1$ is the inside diameter of said cylindrical tube;
$V_2$ is the volume of said cylindrical tube;
$P$ is reference pressure; and
$\Delta P$ is said maximum fluid pressure.

12. An apparatus as defined in claims 1 or 10 further comprising connector means for housing said pressure transducer means therein and for providing electrical connection between said transducer means and an electrical cable.

13. An apparatus as defined in claim 12 wherein said pressure transducer means comprises a piezoresistive semiconductor integrated circuit having a diaphragm for deflection in response to fluid pressures exerted on one side of said diaphragm, and said connector means comprising means for continuously venting an opposite side of said diaphragm to a reference pressure.

14. An apparatus as defined in claim 13 wherein said connector means comprises a valve means for selective positioning between a first and a second position such that when said valve means is in said first position, said one side of said diaphragm is vented through said connector means to said reference pressure, and when said valve means is in said second position, said one side of said diaphragm is in fluid communication with fluid pressures communicated through said second chamber means.

15. An apparatus as defined in claim 14 wherein said connector means further comprises means for releasably retaining said valve means in the position to which it is selectively moved.

16. An apparatus as defined in claim 12 wherein said connector means comprises means for receiving and securing a proximal end of said catheter in a fluid-tight fit.

17. An apparatus as defined in claim 16 wherein said connector means comprises a fluid port through which fluids are infused into and through which fluid samples are withdrawn from said second lumen, and wherein said receiving and securing means comprises means for orienting said second lumen in a selected position relative to said fluid port so that an aperture formed through said catheter will provide fluid communication between said second lumen and said fluid port.

18. An apparatus for continuously measuring intrauterine fluid pressures exerted by amniotic fluid within a uterus, comprising:
   a catheter for insertion into said uterus so as to detect said pressures, said catheter comprising a first chamber formed in a distal end of said catheter at the interior thereof for defining a first volume, said catheter further comprising a plurality of apertures formed at said distal end of the catheter for providing fluid communication between said amniotic fluid in the uterus and said first chamber such that amniotic fluid will enter said first chamber and form a liquid column therein having a liquid-air interface, and said catheter further comprising a second chamber formed within the interior of said catheter for defining a second volume, said second chamber being air-filled, and wherein a ratio is defined by said first and second volumes such that the ratio of said first volume to said second volume is such that at maximum fluid pressure exerted during a contraction of the uterus, said liquid column will tend to be minimized so as to minimize hydrostatic pressure error resulting therefrom and such that said liquid-air interface will not enter said second chamber; and a pressure transducer means for generating an electrical signal proportional to said fluid pressures communicated to said transducer from said second chamber of the catheter.

19. An apparatus as defined in claim 18 wherein said second chamber comprises a lumen formed in the interior of said catheter and extending throughout a substantial portion of the length thereof, said lumen terminating at a distal end thereof, and wherein said first chamber comprises at least a portion of the interior space of said catheter defined between said distal end of said lumen and a distal end of said catheter.

20. An apparatus as defined in claim 19 further comprising infusion and sampling means for infusing fluid into said uterus and for withdrawing fluid samples from said uterus, as desired.

21. An apparatus as defined in claim 20 wherein said infusion and sampling means comprises a second lumen formed through the interior of said catheter.

22. An apparatus as defined in claim 21 wherein said second lumen is coextensive in length with said lumen of said second chamber.

23. An apparatus as defined in claim 22 wherein said second lumen is sealed at a distal end thereof to prevent fluid communication between said first chamber and said second lumen.

24. An apparatus as defined in claim 23 wherein said catheter comprises a plurality of apertures formed therein for providing fluid communication between said amniotic fluid and said second lumen.

25. An apparatus as defined in claim 21 wherein said lumen of said second chamber comprises a cylindrical tube formed along an interior wall of said catheter, and wherein said second lumen is formed by the remaining space between said cylindrical tube and said interior catheter wall.

26. An apparatus as defined in claim 25 wherein said ratio of said first and second volumes is selected in accordance with the following expression wherein $\Delta I$ is a value that indicates that the liquid-air interface will not enter said second chamber $$\Delta I = (4/\pi)(D_1^2)(V_1 + V_2(1 - P/(P + \Delta P)))$$

where
$\Delta I$ is the change in position within said first chamber of said liquid-air interface;
$V_1$ is the volume of said first chamber means;
$D_1$ is the inside diameter of said cylindrical tube;
$V_2$ is the volume of said cylindrical tube;
$P$ is atmospheric pressure; and
$\Delta P$ is said maximum intrauterine fluid pressure.

27. An apparatus as defined in claims 18 or 25 further comprising connector means for housing said pressure transducer therein and for providing electrical connection between said transducer and an electrical cable.

28. An apparatus as defined in claim 27 wherein said pressure transducer comprises a piezoresistive semiconductor integrated circuit having a diaphragm for deflection in response to intrauterine fluid pressures exerted on one side of said diaphragm, and said connector means comprising means for continuously venting an opposite side of said diaphragm to atmospheric pressure.

29. An apparatus as defined in claim 28 wherein said connector means comprises a valve means for selective positioning between a first and a second position such that when said valve means is in said first position, said one side of said diaphragm is vented through said connector means to said atmospheric pressure, and when said valve means is in said second position, said one side of said diaphragm is in fluid communication with intrauterine fluid pressures communicated through said second chamber.

30. An apparatus as defined in claim 29 wherein said connector means further comprises means for releasably retaining said valve means in the position to which it is selectively moved.

31. An apparatus as defined in claim 27 wherein said connector means comprises means for receiving and securing a proximal end of said catheter in a fluid-tight fit.

32. An apparatus as defined in claim 31 wherein said connector means comprises a fluid port through which amniotic fluids are infused into and through which amniotic fluid samples are withdrawn from said second lumen, and wherein said receiving and securing means comprises means for orienting said second lumen in a selected position relative to said fluid port so that an aperture formed through said catheter will provide fluid communication between said second lumen and said fluid port.

33. An apparatus for continuously measuring intrauterine fluid pressures exerted by amniotic fluid within a uterus, comprising:
a catheter for insertion into said uterus so as to detect said fluid pressures, said catheter comprising a cylindrical tube formed along an interior wall of said catheter so as form a first lumen which extends throughout a substantial portion of the interior length of said catheter, said first lumen terminating at a distal end thereof a selected distance from a distal end of said catheter such that a chamber is formed in at least a portion of the interior space of said catheter defined by the space between the distal end of said first lumen and the distal end of said catheter, said chamber defining a first volume, and said first lumen defining a second volume, said catheter further comprising a second lumen formed in the remaining space between said cylindrical tube and said interior catheter wall and said second lumen being coextensive in length with said first lumen and said second lumen being sealed at a distal end thereof to prevent fluid communication between said chamber and said second lumen, said catheter further comprising a first plurality of apertures formed at said distal end of said catheter to provide fluid communication between said amniotic fluid and said chamber, and further comprising a second plurality of apertures formed through said catheter to provide fluid communication between said amniotic fluid and said second lumen;
a piezoresistive semiconductor pressure transducer comprising a pressure diaphragm for deflection in response to intrauterine fluid pressures exerted on one side of said diaphragm; and connector means for housing said pressure transducer therein and for providing electrical connection between said transducer and an electrical cable, said connector means comprising means for continuously venting an opposite side of said diaphragm to atmospheric pressure, and said connector means further comprising a valve means for selective positioning between a first and a second position such that when said valve means is in said first position, said one side of said diaphragm is vented through said connector means to atmospheric pressure, and when said valve means is in said second position, said one side of said diaphragm is in fluid communication with intrauterine fluid pressures communicated through said first lumen, and said connector means further comprising a fluid port through which amniotic fluids are infused into and through which amniotic fluid samples are withdrawn from said second lumen, and wherein fluid communication from said fluid port to said second lumen is provided by an aperture formed through said catheter at a location adjacent said fluid port.

34. An apparatus as defined in claim 33 wherein said first lumen is air-filled and wherein a ratio is defined by said first and second volumes such that the ratio of said first volume to said second volume is such that at maximum intrauterine fluid pressures, a liquid column formed by amniotic fluids entering said chamber will tend to be minimized and said amniotic fluid entering said chamber will be prevented from entering said first lumen.

35. An apparatus as defined in claim 34 wherein said ratio of said first and second volumes is selected in accordance with the following expression wherein $\Delta I$ is a value that indicates that the liquid-air interface will not enter said chamber:

$$\Delta I = 4/(\pi D_1^2)(V_1 + V_2)(1 - P/(P + \Delta P))$$

where
$\Delta I$ is the change in position within said chamber of said liquid-air interface;
$V_1$ is the volume of said chamber;
$D_1$ is the inside diameter of said cylindrical tube;
$V_2$ is the volume of said cylindrical tube;
$P$ is atmospheric pressure; and
$\Delta P$ is said maximum intrauterine fluid pressure.

* * * * *

UNITED STATES PATENT AND TRADEMARK OFFICE
CERTIFICATE OF CORRECTION

PATENT NO. : 4,966,161

DATED : October 30, 1990

INVENTOR(S) : WILLIAM D. WALLACE et al.

It is certified that error appears in the above-identified patent and that said Letters Patent is hereby corrected as shown below:

```
Column 5, line 65, "apparatus" should be --apertures--
Column 7, line 46, "ration" should be --ratio--
Column 8, line 30, "thense" should be --thence--
Column 12, line 3, "cather 12" should be --catheter 12--
```

Signed and Sealed this

Third Day of November, 1992

Attest:

DOUGLAS B. COMER

*Attesting Officer*  Acting Commissioner of Patents and Trademarks